(12) United States Patent
Molino et al.

(10) Patent No.: US 6,500,137 B1
(45) Date of Patent: Dec. 31, 2002

(54) PELVIC REGION ORTHOTIC DEVICE

(76) Inventors: Joseph L. Molino, 2 Aura Dr., Valley Cottage, NY (US) 10989; Michael Rebarber, 28 Buckingham Pl., Glen Rock, NJ (US) 07452

( * ) Notice: Subject to any disclaimer, the term of this patent is extended or adjusted under 35 U.S.C. 154(b) by 0 days.

(21) Appl. No.: 09/942,815

(22) Filed: Aug. 30, 2001

(51) Int. Cl.[7] ................................................ A61F 5/00
(52) U.S. Cl. ....................................... 602/19; 128/96.1
(58) Field of Search ................................. 128/845, 869, 128/872–875, 95.1, 96.1; 602/5, 19

(56) References Cited

U.S. PATENT DOCUMENTS 2,453,370 A * 11/1948 Hittenberger ................. 602/19
2,813,526 A * 11/1957 Beebe ........................... 602/19
2,828,737 A *  4/1958 Hale ............................. 602/19
3,351,053 A * 11/1967 Stuttle .......................... 602/19
3,548,817 A * 12/1970 Mittasch ...................... 602/19
5,363,863 A * 11/1994 Lelli ............................. 602/19

* cited by examiner

Primary Examiner—Michael A. Brown
(74) Attorney, Agent, or Firm—Lawrence G. Fridman

(57) ABSTRACT

A medical device consists of a sacral panel, an abdominal panel and first and second trocanteric pad assemblies positioned therebetween. The sacral panel is adjustably connected to each of the first and second trocanteric pad assemblies by posterior connecting elements. The abdominal panel is adjustably connected to each of the first and second trocanteric pad assemblies by anterior adjusting elements. Upon positioning of the device on a body of a patient, tightening of the anterior adjusting elements generates inwardly directed pressure exerted by the device on a pelvic region of the user.

17 Claims, 11 Drawing Sheets

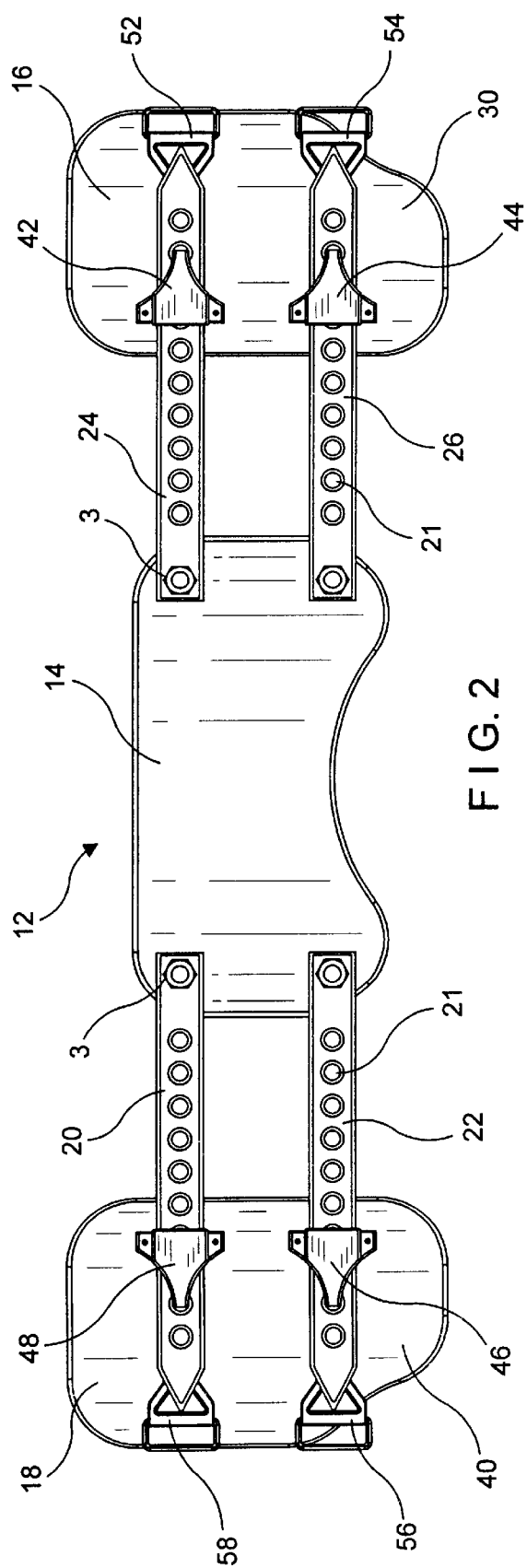
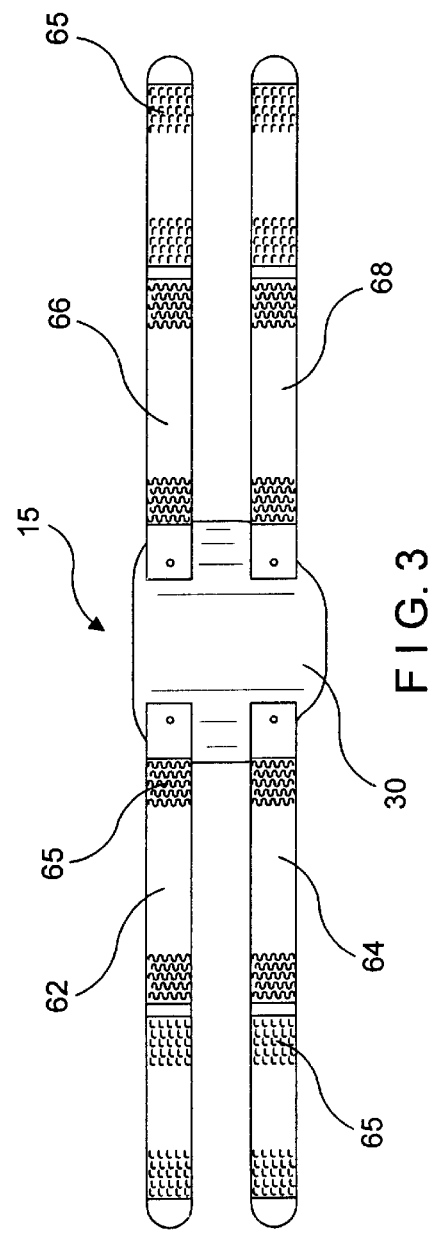
FIG. 2
FIG. 3

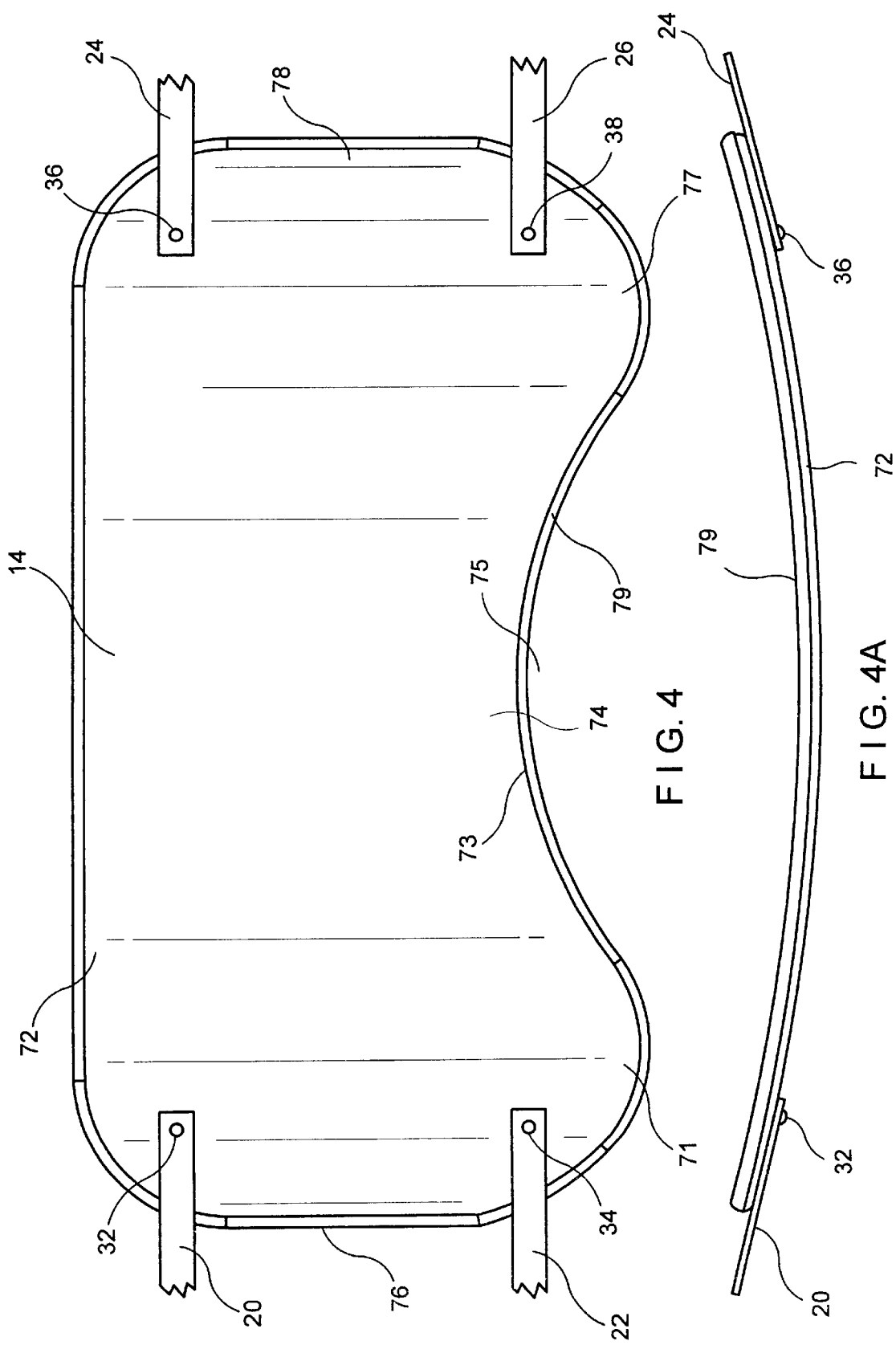

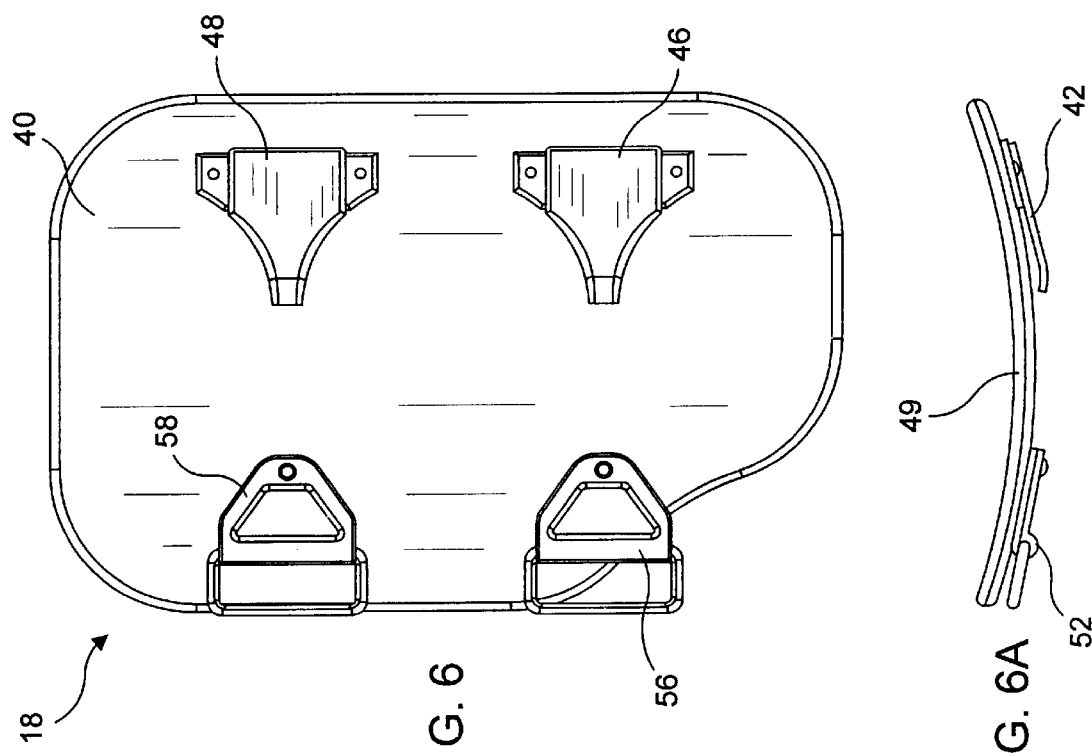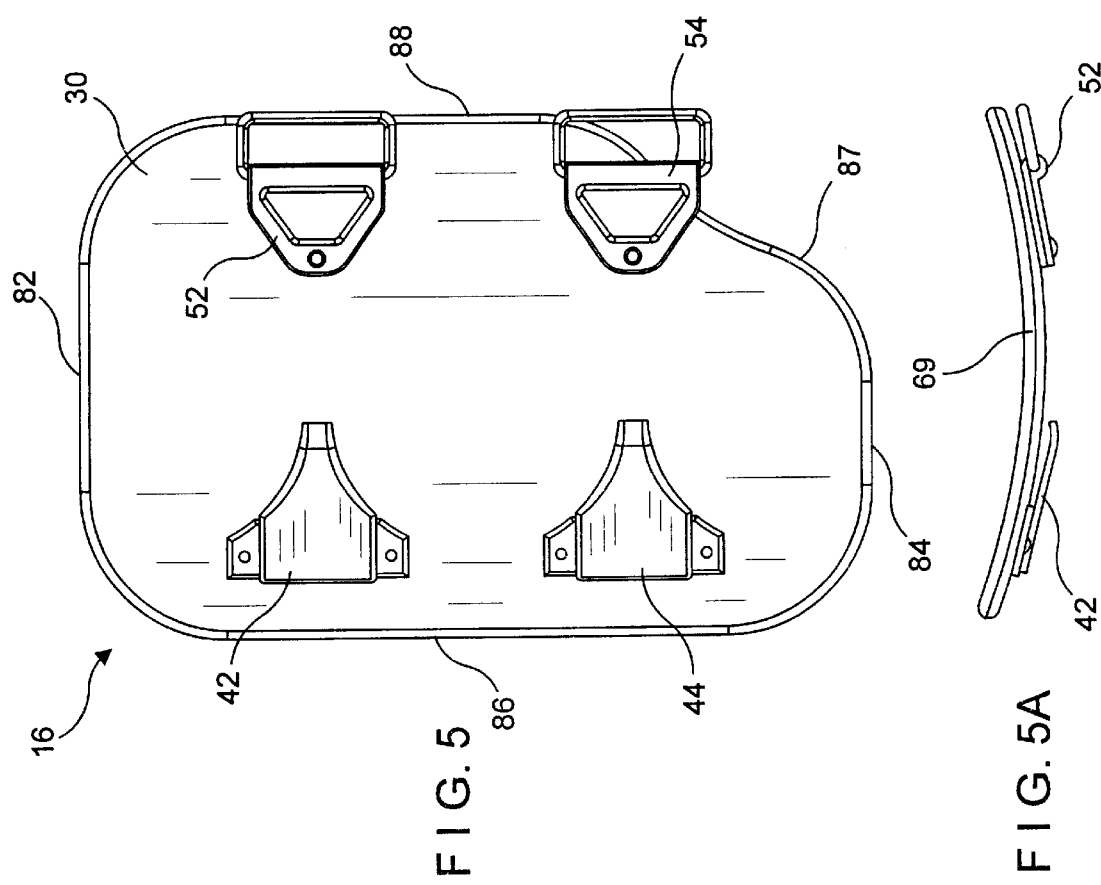

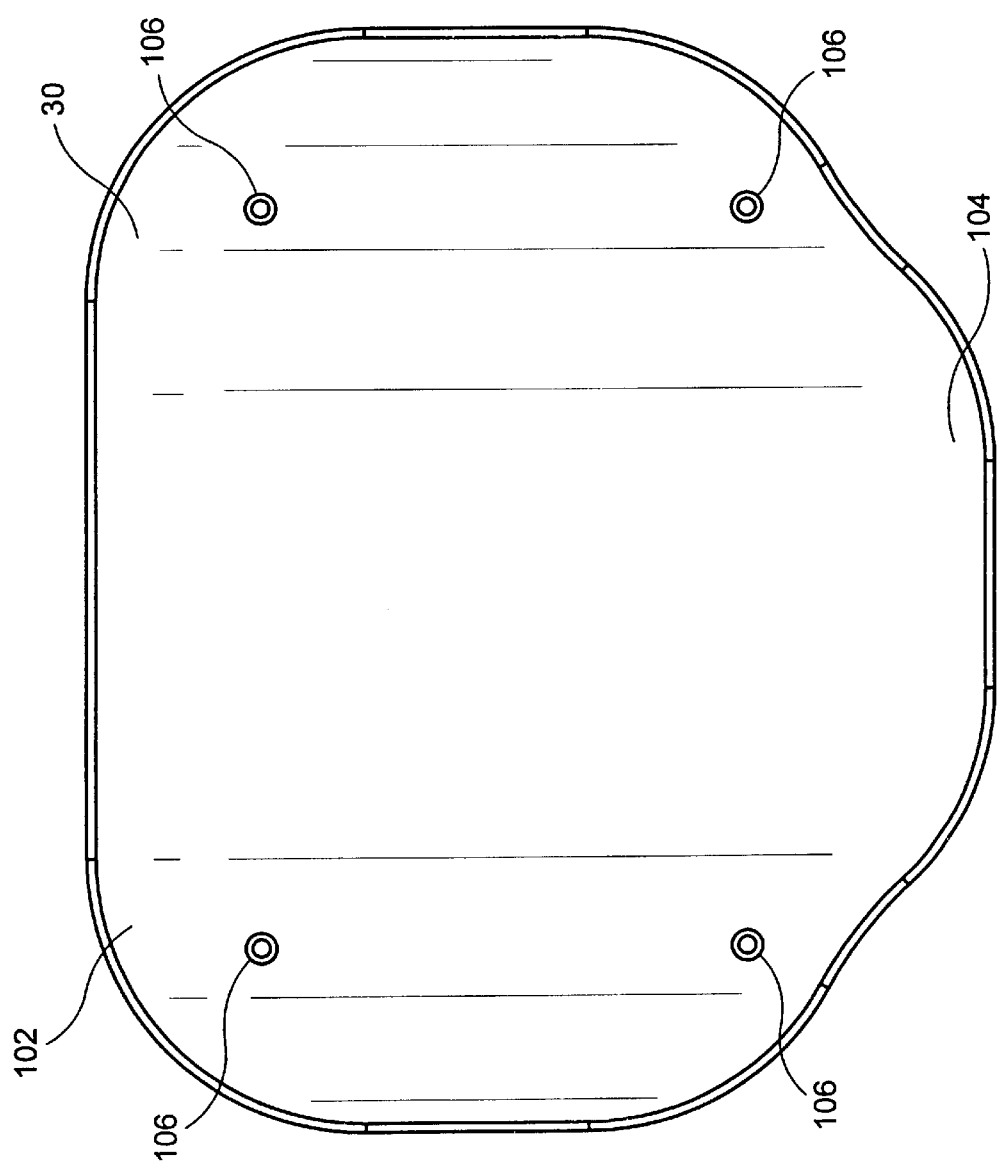
FIG. 8
FIG. 8A

PELVIC REGION ORTHOTIC DEVICE

FIELD OF THE INVENTION

The invention relates to the emergency medicine in general, and specifically it relates to medical devices for maintaining the integrity of the pelvic region of humans.

BACKGROUND OF THE INVENTION

The pelvic region of humans is known to be rich in blood supply and to be substantial in concentration of vital nerves. Patients with abdominal crush injuries or with pelvic fractures require delicate handling by emergency medical personnel. It has been known that even limited uncontrollable movements of patients having pelvic fractures can cause grave damage in the form of puncturing, tearing and stretching of both arterial and venus structures in the pelvic and sacral areas. Such movements can also lead to a substantial and permanent damage of vital nerves in this region of a human body. An example of such medical conditions causing further internal injuries is "an open book fracture". This fracture often leads to a significant movement of bones. As a result, the stability of the pelvis is compromised and it becomes open in a manner similar to opening of a closed book.

The injuries discussed hereinabove can cause significant and permanent damage to the femoral artery and to various nerve structures passing through the pelvis region. In this condition the neighboring venus, arterial and nerve structures can be severely damaged causing a fatality or permanent disability. Therefore, in order to prevent further serious arterial, venus and nerve damage, this region of a human body requires stabilization even prior to a patient being transported to a hospital or other medical facilities.

Thus, it has been a long failed and unsolved need to provide an orthotic device capable of minizing the results of pelvic fractures and can be readily adapted to situations in which significant restriction or immobilization of the pelvic region of a patient is necessary.

SUMMARY OF THE INVENTION

One aspect of the invention provides a medical device consisting of a sacral panel for positioning at a sacral region, first and second trocanteric pad assemblies for positioning at trocanteric regions and an abdominal panel for positioning at an abdominal region of the user. The sacral panel is adjustably connected to each of the first and second trocanteric pad assemblies by at least one posterior connecting element, so that position of each trocanteric pad assembly can be independently adjusted relative to the sacral panel. The abdominal panel is adjustably connected to each of the first and second trocanteric pad assemblies by at least one anterior adjusting element. Upon tightening of the anterior adjusting elements inwardly directed pressure is exerted by the device on the pelvic region of the user.

As to another aspect of the invention, at least one posterior connecting element consists of a pair of posterior connecting elements positioned at each side of the sacral panel for independent adjustment of the position of the trocanteric pad assemblies relative to the sacral panel. Each anterior adjusting element consists of a pair of anterior adjusting elements positioned at each side of the abdominal panel.

As to a further aspect of the invention, the sacral panel is formed by first and second lateral portions spaced from each other. The lateral portions are interconnected by proximal and distal portions. A cut out region is defined at the distal portion, so that upon positioning on the body of a user, a center of the cut out region is positioned at a substantially higher elevation than side areas of the distal portion adjacent to the first and second lateral portions. The downwarldy extending side areas of the distal portions provide support to a lower back, while the cut out portion is positioned above the buttock of the user.

As to still another aspect of the invention, each pair of the posterior connecting elements consists of a proximal posterior connecting element and a distal posterior connecting element. Each proximal connecting element is movably positioned at the proximal portion and each distal posterior connecting element is movably positioned at the distal portion of the sacral panel.

As to still a further aspect of the invention, each trocanteric pad assembly includes proximal and distal posterior adjusting arrangements and proximal and distal anterior adjusting arrangements. The proximal posterior adjusting arrangement is adapted for receiving an adjusting position of the proximal posterior connecting element. The distal posterior adjusting element is adapted for receiving an adjusting position of the distal posterior connecting element. The proximal and distal anterior adjusting arrangements are provided for receiving and adjusting position of the anterior adjusting elements. Each posterior adjusting element is preferably in the form of a clip connected to the respective trocanteric pad and formed with a biasing engagement portion provided for selectively engaging and disengaging the respective posterior connecting element.

Still another aspect of the invention provides a medical device, wherein a circumferentially rigid sub-assembly is formed by the sacral panel, the first and second trocanteric pad assemblies interconnected by the posterior connecting elements, so that tightening of the abdominal adjusting elements generates a predetermined pressure exerted by the trocanteric pads and directed to the center pelvic region.

The device of the invention has been designed to redirect the medial forces forth lateral regions of the trunk of the pelvic area, which are known for their ability to exert pressure over the trocanteric area or the lateral side of the pelvis both on the left and right side. Thus, the present invention is adapted to prevent the pelvic area or the pelvic bone from splaying or from opening up.

The invention provides the ability to adopt the device to accomodate many types of the patients' bodies.

BRIEF DESCRIPTION OF THE DRAWINGS

The preferred embodiment of the invention will hereinafter be described in conjunction with accompanying drawings which are adapted to illustrate and not to limit the invention, wherein:

FIG. 2 is a front elevational view of the sacral panel assembly;

FIG. 3 is a front elevational view of the abdominal panel assembly;

FIG. 4 is a front elevational view of a sacral panel;

FIG. 4A is a top plan view thereof;

FIG. 5 is a front elevational view of one trocanteric pad assembly;

FIG. 5A is a top plan view thereof;

FIG. 6 is an elevational view of another trocanteric pad assembly;

FIG. 6A is a top plan view thereof;

FIG. 8 is an elevational view of an abdominal panel;

FIG. 8A is a top plan view thereof,

DESCRIPTION OF THE PREFERRED EMBODIMENT

Figure 1:
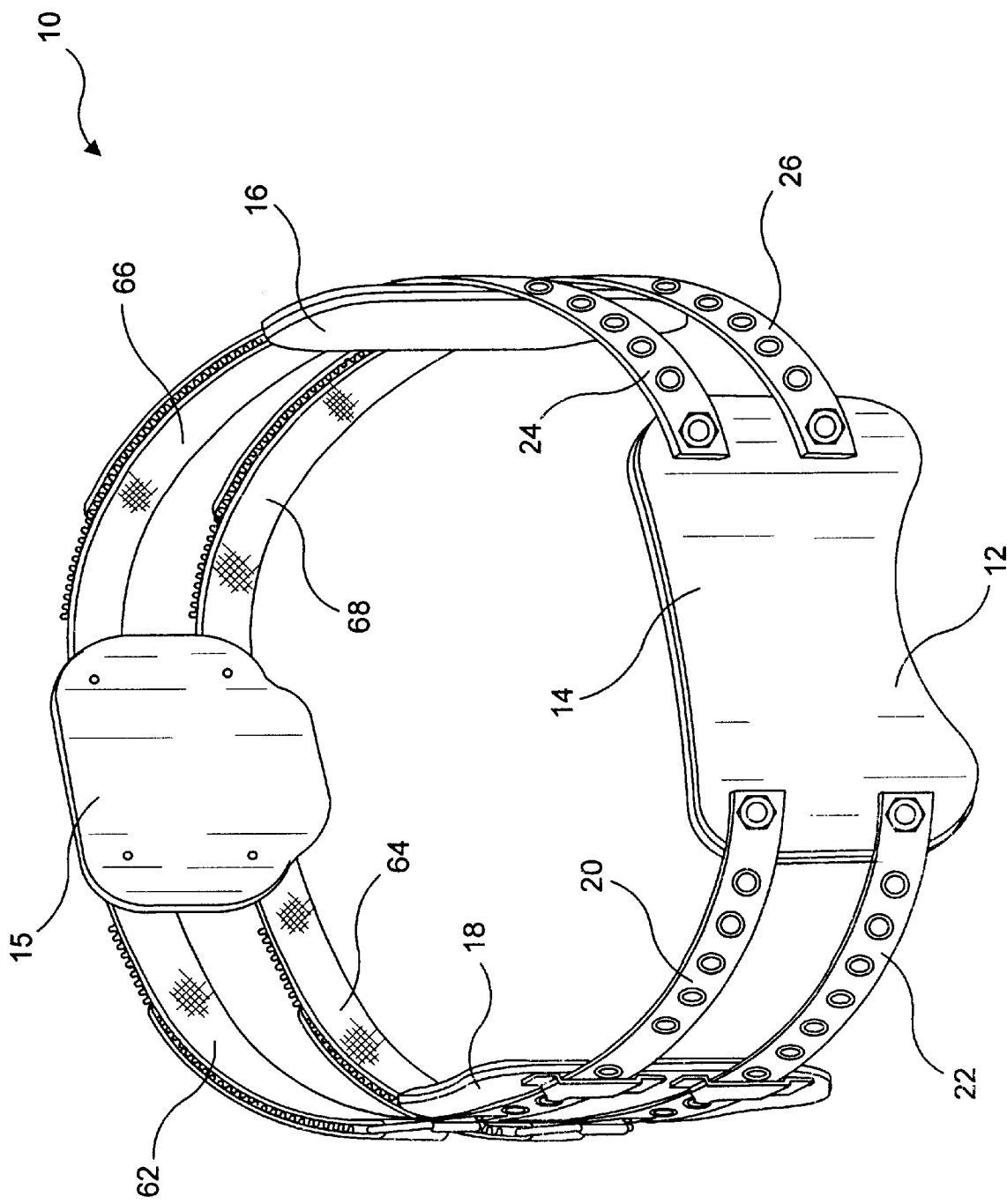
FIG. 1 is a perspective view showing an orthotic device of the invention.

Referring now to FIG. 1 wherein a pelvic area restriction orthotic device 10 of the invention has been illustrated. The device 10 consists of an anterior section or an abdominal panel assembly 15 and a posterior section or a sacral panel assembly 12 with trocanteric pad assemblies 16 and 18 interposed therebetween. Referring now to FIGS. 2 and 4, the assembly 12 is composed of a sacral panel 14 provided for positioning over the sacral area on the posterior lower back of a patient and a plurality of sacral-to-trocanter straps or posterior connecting elements. In the preferred embodiment of the invention four sacral-to-trocanter straps or posterior connecting elements 20, 22, 24 and 26 extend outwardly from the sacral panel. These elements are adapted for adjustably connecting the sacral panel 14 to the first trocanteric pad assembly 16 and the second trocanteric pad assembly 18.

The abdominal panel assembly 15 includes an abdominal panel 30 and a plurality of abdominal straps or anterior adjusting elements connected thereto. As best illustrated on FIGS. 1 and 3, in the preferred embodiment of the invention there are provided four abdominal straps or anterior adjusting elements 62, 64, 66 and 68. As will be described in more detail hereinbelow, one of the main functions of the abdominal straps or anterior adjusting elements is to provide connection between the abdominal panel 30 and the trocanteric pad assemblies 16 and 18. Furthermore, after the entire orthotic device 10 has been properly positioned and fitted to accommodate a specific body of a patient, many adjustments are accomplished through cooperation of the anterior adjusting elements with respective adjustment members forming a part of the trocanteric pad assemblies 16 and 18.

As best illustrated in FIGS. 1, 2 and 4, the sacral panel 14 is slightly curved in the anterior to posterior direction to mimic the natural curvature of a human body. To maintain this shape, the sacral panel 14 is made of a light and substantially rigid plastic material. A layer of soft padding 79 can be provided on the inner surface of the panel 14 for comfort and convenience. The sacral panel 14 is formed with slightly rounded and spaced from each other 9 first lateral portion 76 and a second lateral portion 78 which are interconnected by a proximal portion 72 and a distal portion 74. An arc-shaped cut out region 75 is formed at the distal portion 74. While positioned on a body of a patient, a central area 73 of the cut-out is located at a substantially higher elevation than side regions thereof 71 and 77. The downwardly extending side regions 71 and 77 are adapted to provide the required support for the lower back, while the central area 73 of the cut-out region 75 is typically positioned over and above the buttocks of a patient. In such orientation a user, while wearing the orthotic device 10, is able to enjoy toilet privileges without soiling or contaminating the sacral panel 14.

To facilitate attachment of the posterior connecting elements, in the preferred embodiment at least four openings 32, 34, 36 and 38 are preferably formed within the panel 14. The openings 32 and 36 are positioned at the proximal portion 72, whereas the openings 34 and 38 are positioned at the distal portion 74. The proximal posterior connecting elements 20 and 24 are movably or pivotably attached at the proximal portion 72, near the respective lateral portions 76, 78 of the sacral panel 14. In a similar manner, the distal posterior connecting elements 22 and 26 are movably or pivotably positioned at the distal portion 74 in the vicinity of the lateral portions 76, 78, respectively.

This attachment can be accomplished by means of rivets or any other conventional fasteners.

In the preferred embodiment of the invention, to facilitate adjustment of the trocanteric pad assemblies 16 and 18 relative to the sacral panel 14, the connecting elements can be formed with a plurality of apertures 21 which are adapted for cooperation with first adjustment devices or adjustment clips 41, 44, 46 and 48. The posterior connecting elements 20, 22, 24 and 26 are made of a flexible material which is not subject to longitudinal elongation or expansion when longitudinally directed forces are applied thereto.

As best illustrated in FIGS. 2 and 5, the first trocanteric pad assembly 16 consists of the first trocanteric pad 30 formed with two pairs of adjustment elements. The trocanteric pad 30 is formed having substantially vertical lateral parts 86 and 88 and properly curved proximal part 82 and distal part 84. The second trocanteric pad 40 is of similar design. In each trocanteric pad a distal anterior corner has been removed, so that a side portion extends at an angle to the respective lateral and distal sides. In this respect FIG. 5 clearly shows that the side portion 87 is positioned at an angle to the distal side 84 and lateral side 88. Such design minimizes interference of the trocanteric pads with the bones of the hip and eliminates the discomfort, especially when the orthotic device 10 is utilized while a user is in a sitting or semi-reclined position.

In the first trocanteric pad assembly 16, the first pair of adjustment elements includes a proximal posterior adjustment member or clip 42 which is adapted for receiving and controlled adjustment of the proximal posterior connecting element 24 and an adjustment chafe 52 is provided for cooperation with and adjustment of a proximal anterior adjusting element 66. The elements 42 and 52 are positioned at the proximal region 82 of the trocanteric pad 30. In a similar manner, the second pair of adjustment elements consist of the distal posterior adjustment member or clip 44 provided for controlled adjustment of the distal posterior connecting element 26 and a chafe 54 designed for receiving an adjustment of the distal anterior adjusting element 68. The members 44 and 54 are positioned at the distal region 84 of the pad 30.

Similar to the above-discussed arrangement, in the preferred embodiment of the invention, the second trocanteric pad assembly 18 includes a second trocanteric pad 40 which is also formed with two pairs of adjustment members. The proximal posterior adjustment clip or member 48 and the chafe 58 are equidistantly spaced from the proximal region of the pad 40, whereas the distal posterior adjustment member or clip 46 and the chafe 56 are similarly positioned with respect to the distal region of the pad 40. The adjustment member 48 adjustably receives the proximal posterior strap or connecting element 20, whereas the chafe 58 receives and provides the adjustment of the anterior adjusting element 62. On the other hand, the adjustment member 46 adjustably receives the distal posterior strap or connecting element 22 and the chafe 56 is provided to facilitate adjustment of the distal anterior adjusting element 66.

Similar to the sacral panel 34, the first and second trocanteric pads 16 and 18 are formed with a slight curvature to mimic the natural shape of a human body. A soft padding 89, 49 can be provided at the inner surface of these pads for comfort and convenience of a wearer.

Figure 11:
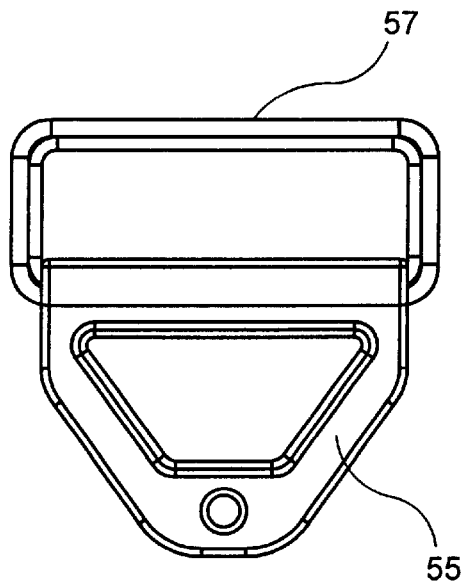
FIG. 11 is a plan elevational view of the chafe assembly.

As best illustrated in FIG. 11 each chafe consists of an anchor arrangement 55 adapted for its permanent attachment to the exterior surface of the respective trocanteric pad. A ring 57 to facilitate insertion and handling of the respective anterior adjustment elements and is adjustably received by the anchor 55. The shape of the ring 57 is adapted to accomodate the shape of the respective anterior adjustment element.

As best illustrated in FIGS. 2, 5, 9, and 10, the adjustment members 42, 44, 46 and 48 are of the similar design. A typical adjustment member consists of a main body 92 which narrows in the direction from a rear portion 97 to a front portion 93. Thus, the width of the front engaging portion 93 is substantially narrower than the width of the rear portion 97. The connecting shoulders 94 and 95 extend outwardly from the main body 92 at the rear portion 97. Each shoulder is formed with at least one opening 91. In the assembled condition of the device, each opening 91 receives a fastener adapted for permanent attachment of the adjustment clip to the outer surface of the respective trocanteric pad. The body 92 in general and the front portion 93 specifically are made of a resilient material capable of performing a biasing or spring function. It is clearly illustrated in FIGS. 7 and 8 that the elevation of the front tip of the engaging portion 93 is substantially lower than the elevation of the rest of the body 92. Thus, in operation, in view of the controllable biasing or spring function, the engaging tip of the front portion 93 is capable of engaging and disengaging the apertures 21 formed in the posterior connecting elements 20, 22, 24 and 26.

Figure 10:
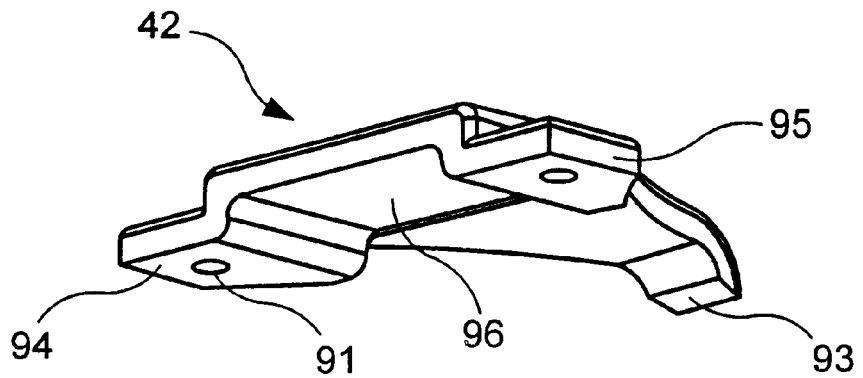
FIG. 10 is a bottom perspective view of the adjustment clip shown in FIG. 7.

Referring now to FIG. 10, wherein the interior area of the adjustment members 42, 44, 46 and 48 is best illustrated. The inner side walls of the connecting shoulders 94 and 95 and an inner wall of the body 92 form a C-shaped channel adapted to slidably receive the respective posterior connecting element. Thus, in order to provide adjustment of the trocanteric pads 16 and 18 relative to the sacral panel 14, the engaging tip of the front engaging portion 93 is lifted, so as to disengage the apertures 21 in the respective connecting elements or straps. Thus, the straps or connecting elements can slide within the C-shaped channel and between the inner area of the adjustment clip and the outer surface of the respective trocanteric pad. When the desired position of posterior connecting element is achieved, the engaging tip is released, so as to engage the respective aperture 21.

Figure 7A:
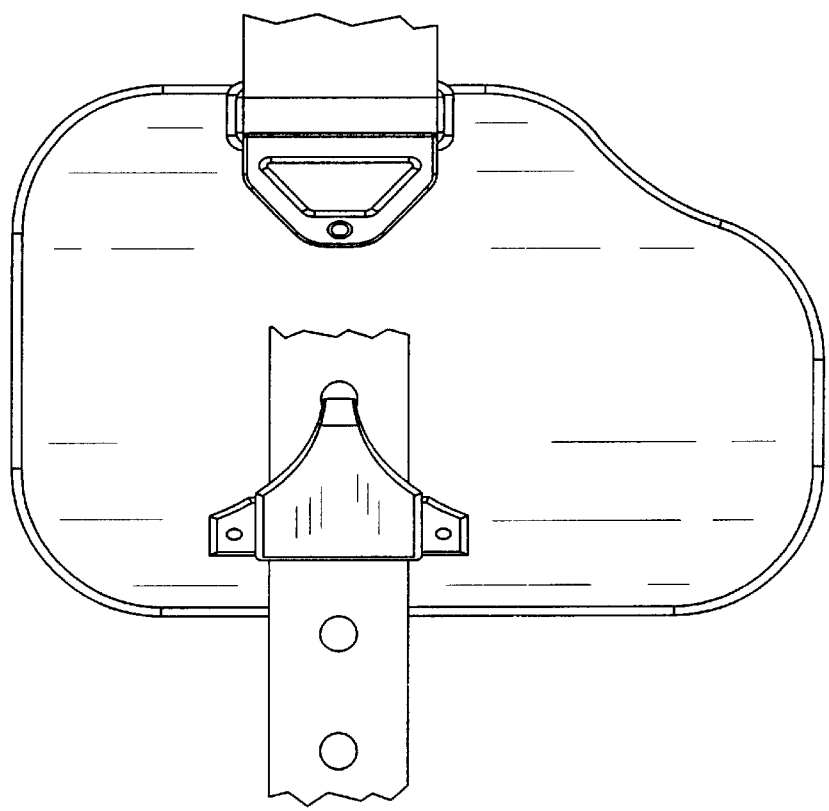
FIG. 7A is an elevational view of a further embodiment of the trocanteric pad assembly.
Figure 7:
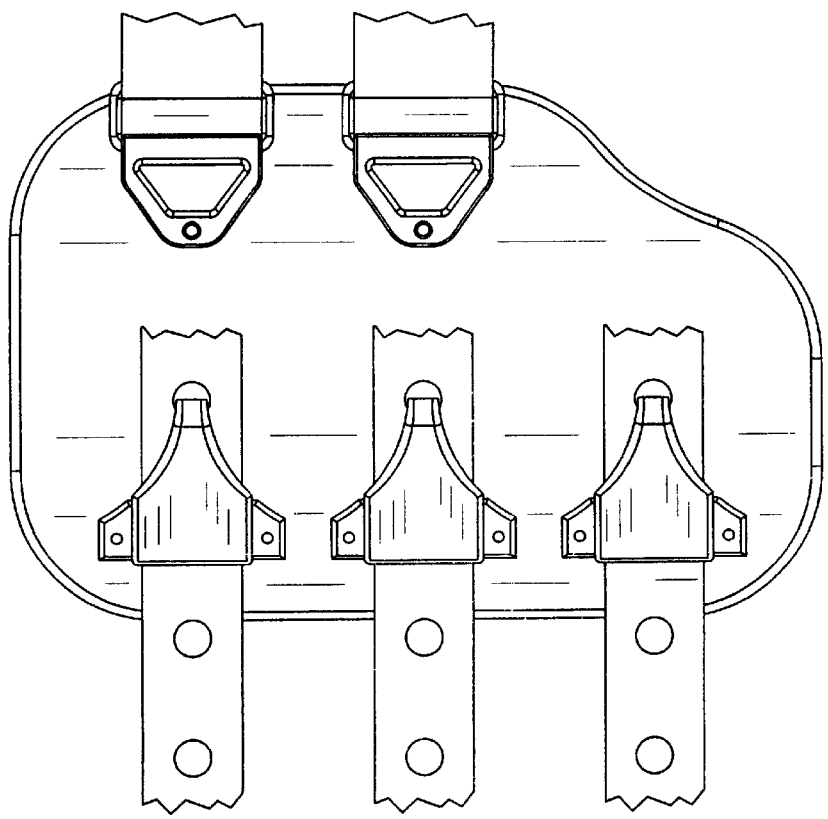
FIG. 7 is an elevational view of another embodiment of the trocanteric pad assembly.
Figure 9:
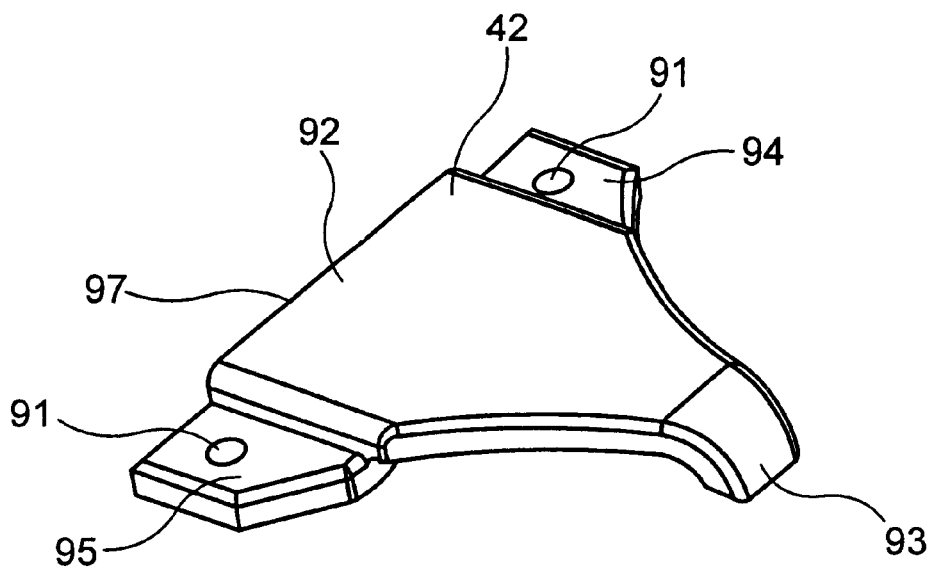
FIG. 9 is a top perspective view of an adjustment clip of the trocanteric pad.

Although the specific configuration of the adjustment members has been described hereinabove, it should be understood that other designs thereof capable of slidably receiving a connecting element and controllably engaging and disengaging its body, is within the scope of the invention. Furthermore, in the preferred embodiment of the invention the trocanteric pad assemblies have been described having two sets of the distal posterior adjustment elements or clips and chafes. However, the trocanteric pad assemblies having any other reasonable number of these elements is also contemplated. For example, FIG. 7 illustrates the trocanteric pad formed with three posterior adjustment members and two chafes, whereas with the embodiment of FIG. 7A the trocanteric pad contains one posterior adjustment member and one chafe.

Turning now to FIGS. 1, 3 and 8, wherein the abdominal panel 30 is best illustrated. The distal portion 104 the abdominal panel 30 tapers down, so that the width of its proximal portion 102 is substantially wider than that of the distal portion thereof 104. There are at least four openings 106 formed within the abdominal panel for attachment of the abdominal straps or anterior adjustment elements 62, 64, 66 and 68. The abdominal panel is made of a flexible material capable of yielding and bending while in use. Upon positioning on a body of a patient, the distal portion 104 does not interfere with the pubic area. In view of the flexibility of the abdominal panel, a patient will be comfortable in a sitting position while wearing the orthotic device of the invention. The design of the orthotic device in general and the abdominal panel specifically allows the patient to assume a semi-inclined or a seated position which enables the patient to wear the orthotic device of the invention during the recuperative process.

As best illustrated in FIG. 3, each anterior adjusting element is a flexible strap having multiple engaging arrangements 65 disposed through its length. In the preferred embodiment the engaging arrangements 65 are in the form of VELCRO strips containing matching hook and loop portions and situated throughout each adjusting element 62, 64, 66 and 68. In use, each adjusting element is inserted into the ring of the respective chafe and bent over, so as to bring the corresponding hook and loop portions into mutual engagement. This facilitates tightening of the adjusting elements to the extent necessary which in turn prevents splaying or opening the pelvic region of a patient. It should be obvious to a person of ordinary skills in the present art that other conventional engagement arrangements are also within the scope of the invention.

Figure 12:
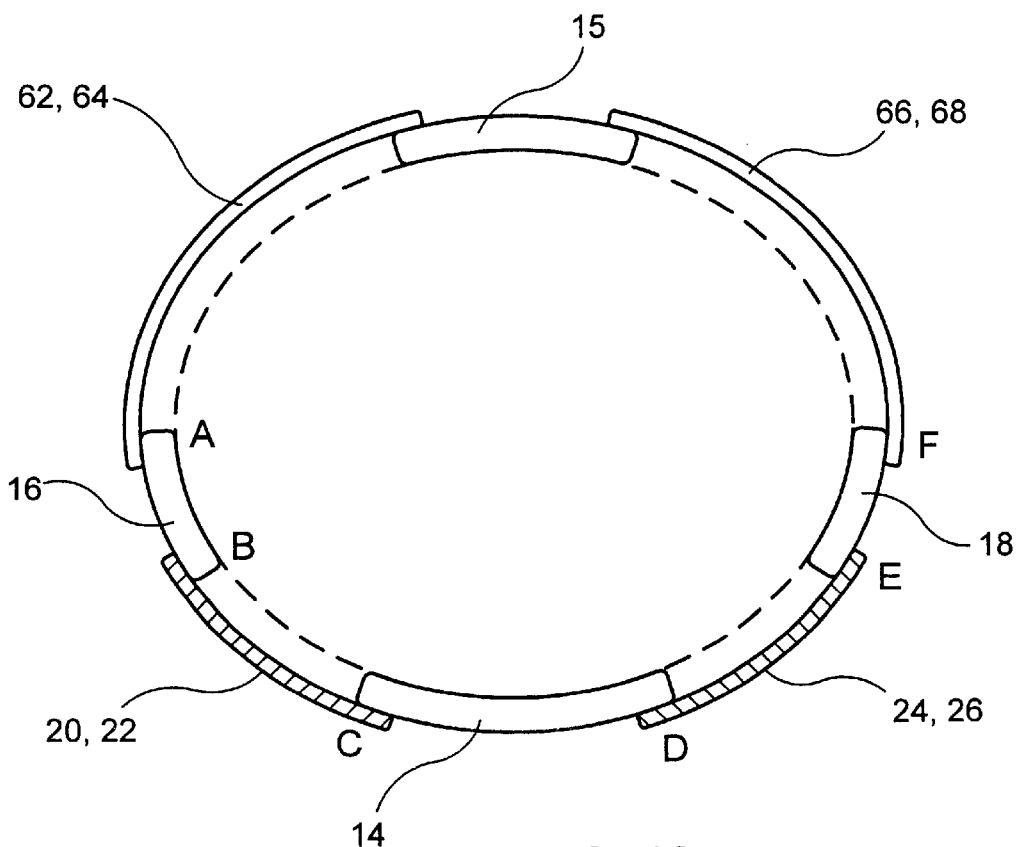
FIG. 12 is a view showing a circumferentially rigid sub-assembly.
Figure 13:
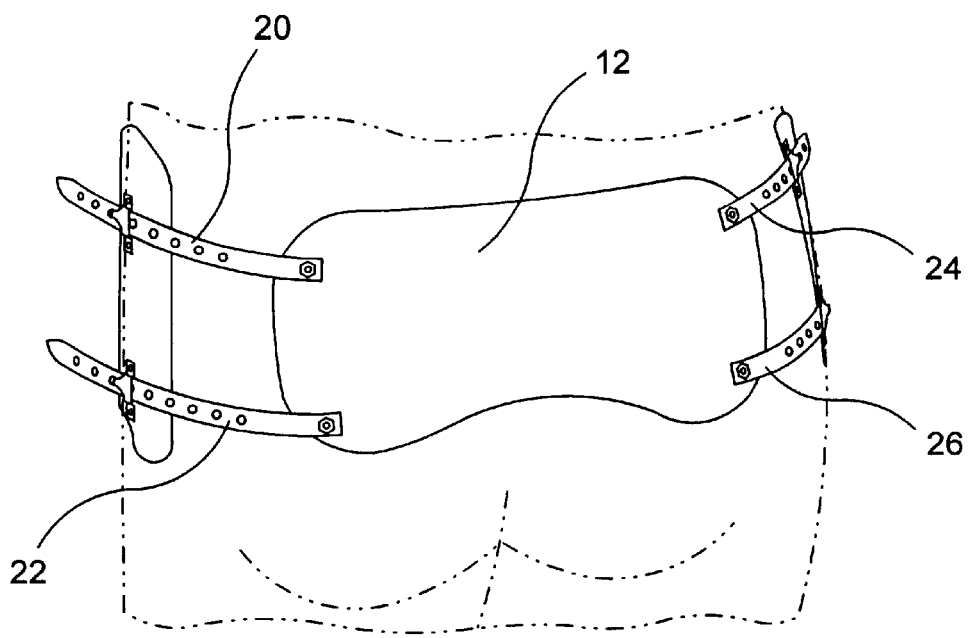
FIG. 13 shows positioning of the sacral panel assembly on a body of a patient.
Figure 14:
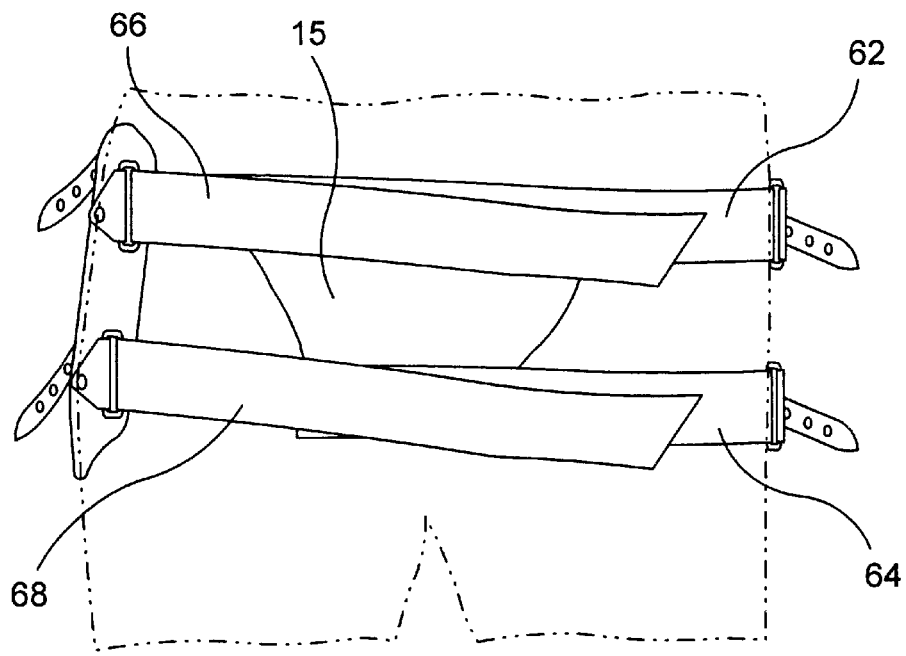
FIG. 14 shows positioning of the abdominal panel assembly on a body of a patient.
Figure 15:
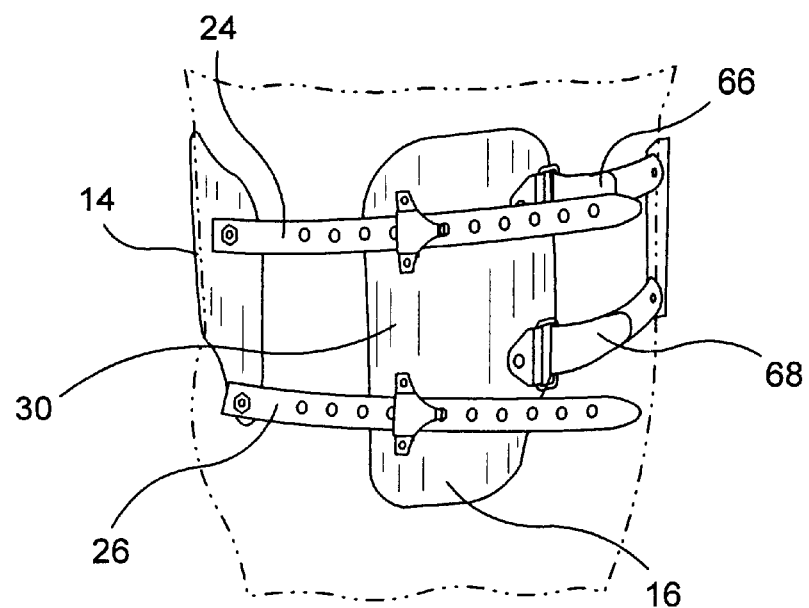
FIG. 15 shows positioning of one trocanteric pad assembly on a body of a patient.
Figure 16:
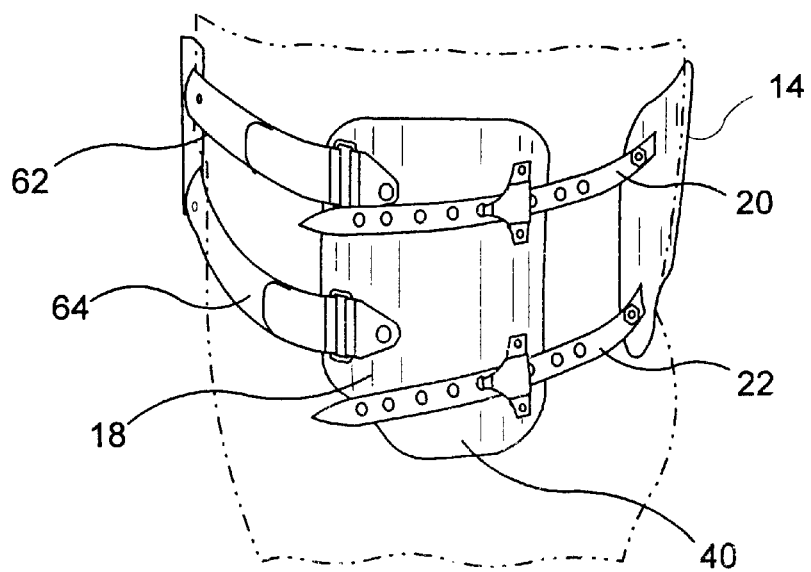
FIG. 16 shows positioning of another trocanteric pad assembly on a body of a patient.

After the orthotic device 10 has been properly positioned and adjusted to fit a specific body of a patient, a circumferentially rigid sub-assembly 120 (see FIG. 12) is formed by the sacral panel 14 and the first and second trocanteric pad assemblies 16 and 18 which are interconnected by the plurality of posterior connecting elements 20, 22, 24, 26. As to the term of circumferential rigidity, after positioning of the sub-assembly 120 on the body of a patient and initial tightening of the abdominal straps or anterior adjusting elements 62,64,66 and 68 the distance taken along the exterior or circumference of the body of a patient between the sacral panel 14 and the trocanteric pad assemblies 16 and 18 (see segments AB, BC, CD, DE and EF) remains virtually unchanged. In this manner, the elements of the sub-assembly 120 form a circumferentially stable base for the entire pelvic region of a human body. Thus, only a limited force generated by tightening of the anterior adjustment elements 62, 64, 66 and 68 is required to keep the device 10 properly positioned on the body of a patient. Since tightening of the anterior adjusting elements causes virtually no extension of the parts forming the sub-assembly 120 in the circumferential direction, such tightening is directly converted into the required pressure exerted by the device in general and the trocanteric pad assemblies 16 and 18 in particular on a body of a patient. The pressure is directed toward the center of the body and prevents undesirable movement and expansion of the pelvic region of a patient.

In the preferred embodiment each trocanteric panel is approximately 8.5 inches in length for a medium to medium/large sized person. Such configuration should provide a significant surface area on the lateral side of the pelvic region to evenly distribute the forces that are necessary to contain the pelvic region. Thus, the pressure exerted by the device is evenly distributed over a substantial area of the patient's body. Since each posterior connecting element is independently adjustable, the length of the distal connecting elements 22 and 26 between the sacral panel and the respective adjustment members 44 and 46 can be longer or shorter than that of the length of their proximal counterparts 20 and 24 and visa versa. In this manner, the orthotic device 10 of the invention can be adjusted for bodies of various patients with and without ubnormalities. For example, the orthotic device 10 can be readly adapted to accomodate patients with significant pelvic developments. As to another example, the hips flair of female patients can be accomodated through adjustment of the posterior connecting elements 20, 22, 24, 26 which can be achieved by means of manipulation of the adjustment members 42, 44, 46, and 48. In this manner, one corner of the trocanteric pad can be positioned further away or closer to the sacral panel 14 than the other corners thereof.

For optimum characteristics the sacral and abdominal panels and the trocanteric pads are preferably formed of a substantially rigid plastic material such as polyethylene, other copolymers, polypropylene, or similar materials sufficiently rigid, so that the panel will retain its shape. Although many substantially rigid plastic materials can be used in the construction of the abovementioned elements, care must be taken to insure that the plastic material is sufficiently strong to minimize the possibility of fracture or deformation. The material should also be sufficiently inert to possess no irritating characteristics that can cause skin irritation or rashes. It should be apparent that the sacral, abdominal panels and trocanteric pads may be extruded, vacuum formed, molded or otherwise formed by any suitable process.

A layer of a resilient padding is preferably provided adjacent to the concave inside surfaces of the panels and pads, so as to space the body of the patient from direct contact with such inner surfaces thereof. Such padding is preferably made of a relatively soft resilient material such as closed cell foam rubber or a sponge-like material. In addition to comfort and convenience, the padding assures that an impact against the outside surface of the panel will not be transferred to the body. This is an important consideration when the orthotic device 10 is applied in the emergency situations, for example, at the site of a car accident. Depending upon the porosity of the material utilized for the resilient padding, multiple apertures may or may not be necessary to facilitate ventilation to the body. While apertures in the padding need not be aligned with the apertures in the panel, such alignment could be beneficial.

In the preferred embodiment of the device of the invention all panels, straps, fasteners, clips and chafes are made from a material permeable to X-rays, and is completely radiationally lucent. This enables radiologists to make an accurate diagnosis without interference from appliances made from impermeable to X-rays materials that are typically associated with devices of this nature.

The proper positioning of the elements of the orthotic device 10 is best illustrated in FIGS. 13–16. In use, a patient is initially placed in the safest and most convenient position to receive the sacral panel 14. Typically, the patient is positioned on his or her back or a side. The sacral panel 14 can be slipped underneath the back of the patient, so that he or she does not have to be moved in order to apply the remaining parts of the device. In order to provide connection between the trocanteric pads 16 and 18 and the respective posterior connecting elements 20, 22, 24 and 26, the front engaging portions of the respective adjustment members should be lifted, so as to facilitate sliding of the connecting elements or straps. Such sliding motion is being continued until the first and second trocanteric pads are positioned laterally on the midline of both the left and right side of the patient's body (see FIGS. 15 and 16). Then, the engaging portions of the adjustment elements are released to provide engagement with the apertures 21 of the posterior connecting elements, and lock the pads 16 and 18 in the proper position.

The abdominal panel 30 is then placed on the abdomen of a patient, and the abdominal straps or anterior adjusting elements 62, 64, 66 and 68 are inserted through the rings 57 of the chafes, 52, 54, 56 and 58 located on the trocanteric pads. The straps are then tightened to ensure the proper positioning of the orthotic device 10 and their position locked by means of engagement arrangements 65.

The abdominal straps 62, 64, 66 and 68 may be tightened to the point that the pelvic area is placed in its normal position, so as to achieve a natural pelvic angle. Tightening of the anterior abdominal straps on both sides of the abdominal panel assembly constrains the lateral spread of the device, and limits the pelvis expansion beyond the predetermined range. Since the abdominal straps are totally adjustable, upon examination of a patient by trained professionals after or during emergency situations, their proper tightness can be easily ascertained again. Tightening of the abdominal straps or adjusting elements causes tightening of the entire device and increases the circumferential pressure that is exerted upon the pelvic, abdominal and sacral regions of a patient. Lateral pressure is medially directed by transferring the medially directed force to the trocanteric area, which in turn directs the medial force to maintain closure of the pelvis and pubic ramus area. On the other hand, as the abdominal straps or adjusting elements are loosened, the circumferencial pressure around the pelvic region is reduced. When the adjustment elements are disengaged, the continuity between the sacral panel and the trocanteric pads is interrupted. At this point each trocanteric pad can be disengaged from the respective posterior connecting elements and the sacral panel can be removed.

Figure 18A:
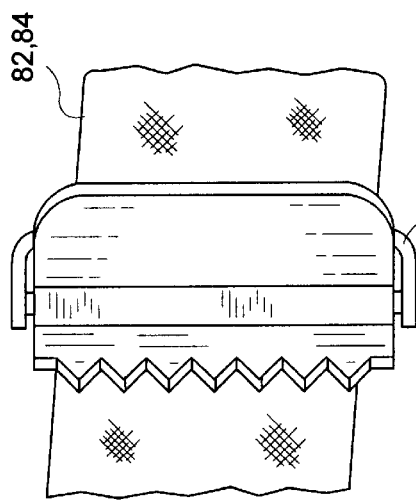
FIGS. 18A and 18B show a closure arrangement of the orthotic device of FIG. 17 in open and closed positions.
Figure 18B:
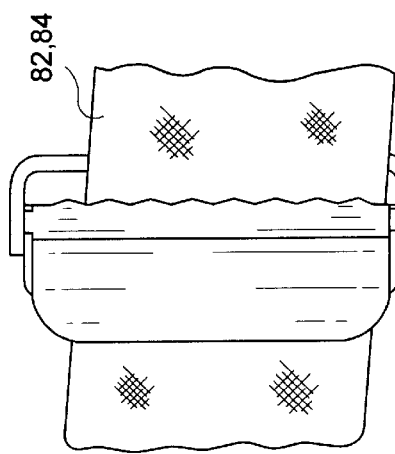
Figure 17:
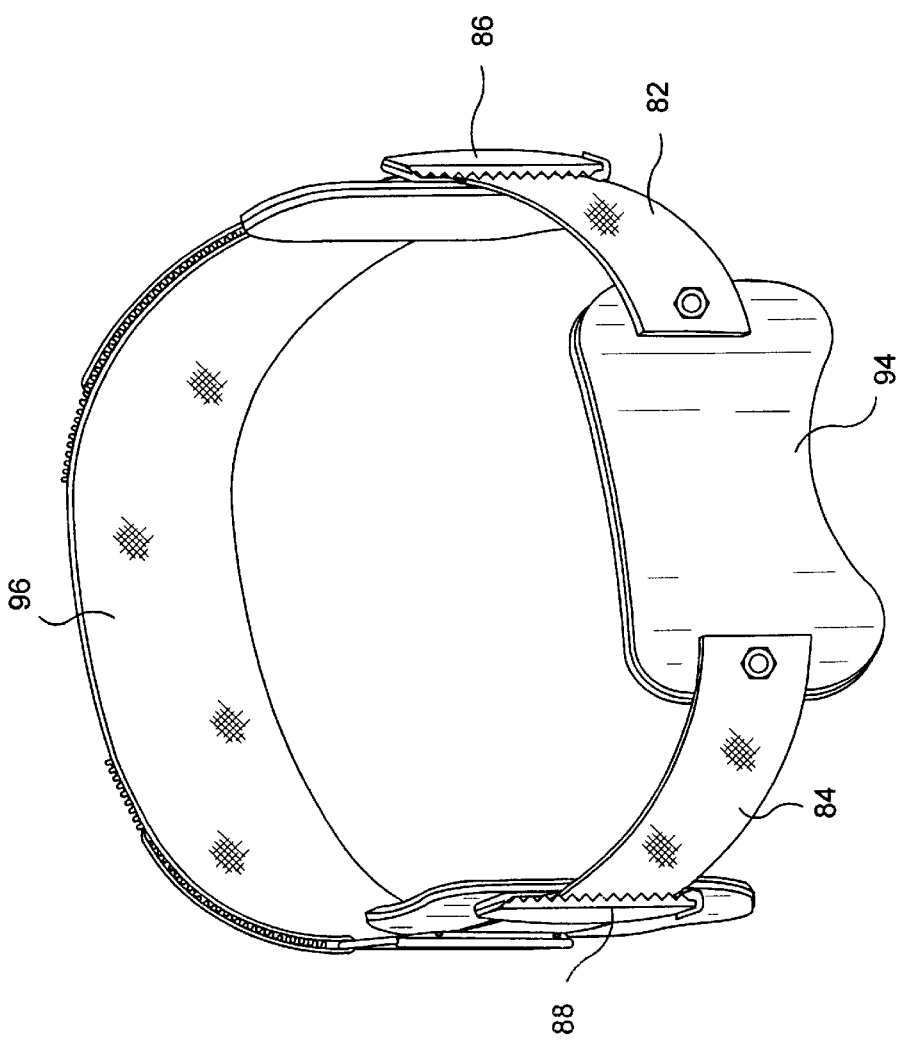
FIG. 17 is a perspective view showing another embodiment of the orthotic device.

Tuning now to FIGS. 17, 18A and 18B which illustrate another embodiment of the invention. As to the connection between each trocanteric pad and the sacral panel a single wide connecting band 82, 84 is utilized, instead of a pair of individual straps or posterior connecting elements. As illustrated in FIG. 17, the connecting bands 82 84 extend outwardly from the lateral portions of the sacral panel 94 in the opposite directions. Each of the trocanteric pads is provided with a closure device 86, 88 adapted to engage and lock the respective band to accommodate a body of a particular patient. In this condition, the closure devices and the connecting bands can be positioned at an angle to each other. Thus, the trocanteric pads can be adjusted in relation to the band on an angular basis on both lateral sides. Position of each individual connecting band can be adjusted to have various lengths, so as to accommodate different shapes of patients' bodies, including the flair of female hips. In the embodiment of FIG. 17, one abdominal broad band 96 extends between the first and second trocanteric pads traversing the abdominal region of a patient. The substantial width of the band provides sufficient engagement and support with the abdominal area of the patient eliminating the need for a separate abdominal panel.

Although the primary fimction of the device of the invention is to minimize results of the pelvic fractures, it can also be readily adapted in other situations where significant restriction or immobilization of the pelvic region is necessary. In this manner the principles of the device of the invention can be utilized in many types of hip or lower back injuries.

Although the invention has been described with reference to the specific embodiments, those skilled in the art will recognize that changes can be made in the form and detail without departing from the spirit and scope of the invention. By way of example, it has been indicated that a pair of posterior connecting elements is provided for adjusting positioning of the trocanteric pad assemblies relative to the sacral panel. However, it should be noted that any reasonable number of posterior connecting elements can be utilized for this purpose. For example, FIG. 7 shows the trocanteric pad with three posterior connecting elements and FIG. 6 illustrates the arrangement with one posterior connecting element. Furthermore, according to the above-discussed embodiment, each posterior connecting element is formed with a plurality of apertures 21 adapted for engagement with the adjustment element. Nevertheless, other ways of cooperation between the posterior connecting elements and adjusting members are contemplated. In this respect, the posterior connecting elements can be formed without the apertures, so that the frictional controlled engagement between the connecting elements and adjusting members is exercised.

What is claimed is:

1. A medical device, comprising:
   a sacral panel for positioning at a sacral region of a user, first and second trocanteric pad assemblies for positioning at trocanteric regions of the user, said sacral panel is adjustably connected to each said first and second trocanteric pad assemblies by at least one posterior connecting element;
   an abdominal panel for positioning at an abdominal region of the user; and
   each said trocanteric pad assembly including spaced from each other at least a pair of posterior adjustment elements, each said posterior adjustment element having a biasing engagement portion for selectively engaging and disengaging the respective posterior connecting element.

2. The medical device according to claim 1, wherein said sacral panel is adjustably connected to each said first and second trocanteric pad assemblies through a pair of posterior connecting elements and said abdominal panel is adjustably connected to each said trocanteric pad assemblies through at least one anterior adjusting element.

3. The medical device according to claim 2, wherein said at least one anterior adjusting element consists of a pair of anterior adjusting elements, each said pair of the anterior adjusting elements is positioned at each side of the abdominal panel and is adapted to receive a pair of anterior connecting elements extending between said abdominal panel and the respective trocanteric pad assembly, upon tightening of said anterior connecting elements inwardly directed force is exerted by said first and second trocanteric pad assemblies on the pelvic region of the user.

4. The medical device as claimed in claim 3, wherein each said posterior connecting elements is made of a flexible material having restricted longitudinal elongation.

5. The medical device as claimed in claim 3, wherein a circumferentially rigid sub-assembly is formed by the sacral panel connected to the first and second trocanteric pad assemblies by the posterior connecting elements, so that tightening of the anterior connecting elements generates a predetermined force exerted by the trocanteric pad assemblies and directed to a center of the pelvic region.

6. The medical device according to claim 3, wherein said anterior connecting elements are pivotably connected to the abdominal panel.

7. The device as claimed in claim 2, wherein each said pair of the posterior connecting elements consists of a proximal posterior connecting element and a distal posterior connecting element, each said proximal posterior connecting element is movably positioned at a proximal portion and each said distal posterior connecting element is movably positioned at a distal portion of the sacral panel.

8. The device as claimed in claim 7, wherein said proximal and distal posterior connecting elements are pivotably connected to the sacral panel.

9. The device according to claim 1, wherein said sacral panel includes first and second lateral portions spaced from each other, said lateral portions being interconnected by proximal and distal portions, a cut out region is defined at the distal portion, so that upon positioning on a body of the user a central area of the cut out region is located at a substantially higher elevation than areas of the distal portion adjacent the first and second lateral portions.

10. The device as claimed in claim 9, wherein the areas of the distal portion adjacent the first and second lateral portions provide support to a lower back, while the cut out region is positioned above buttocks of the user.

11. The medical device as claimed in claim 2, wherein each said trocanteric pad assembly further comprises proximal and distal posterior adjusting arrangements and proximal and distal anterior adjusting arrangements.

12. The medical device as claimed in claim 11, wherein in each said trocanteric pad assembly said proximal posterior adjusting arrangement is adapted for receiving and adjusting the respective proximal posterior connecting element, said distal posterior adjusting element is adapted for receiving and adjusting the respective distal posterior connecting element.

13. The medical device as claimed in claim 12, wherein said proximal and distal anterior adjusting arrangements are adapted for receiving and adjusting the respective anterior connecting elements, so that said proximal and distal anterior adjusting arrangements adjustably receive the proximal and distal anterior connecting elements respectively.

14. The medical device as claimed in claim 11, wherein each said posterior adjusting element is a clip connected to the respective trocanteric pad assembly.

15. The medical device as claimed in claim 14, wherein each said posterior connecting element is formed with a plurality of apertures and said biasing engaging portion is adapted for engagement and disengagement with the apertures formed within the posterior connecting elements.

16. The medical device as claimed in claim 15, wherein each said clip contains a channel formed within an inner portion thereof and is adapted for slidably receiving and guiding movement of the respective posterior connecting element.

17. The medical device as claimed in claim 16, wherein to achieve a predetermined position of each said trocanteric pad assembly on the body of the user the engaging portion of the clip is disengaged, so as to allow movement of the respective posterior connecting element within the channel, said predetermined position is fixed through engagement of the engaging portion with the respective posterior connecting element.

* * * * *